US010165125B2

United States Patent
Govari et al.

(10) Patent No.: US 10,165,125 B2
(45) Date of Patent: Dec. 25, 2018

(54) REMOTE CONTROL AND INTERACTION WITH IMPLANTED DEVICES

(71) Applicant: Biosense Webster (Israel) Ltd., Yokneam (IL)

(72) Inventors: Assaf Govari, Haifa (IL); Yaron Ephrath, Karkur (IL); Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 15/447,449

(22) Filed: Mar. 2, 2017

(65) Prior Publication Data
US 2018/0255184 A1    Sep. 6, 2018

(51) Int. Cl.
| | | |
|---|---|---|
| A61B 5/042 | (2006.01) |
| A61B 5/07 | (2006.01) |
| H04B 5/00 | (2006.01) |
| H04M 11/00 | (2006.01) |
| A61B 5/00 | (2006.01) |
| A61B 5/11 | (2006.01) |
| A61N 1/372 | (2006.01) |
| H04Q 9/00 | (2006.01) |
| H04M 1/02 | (2006.01) |
| H04W 4/02 | (2018.01) |

(52) U.S. Cl.
CPC ......... *H04M 11/007* (2013.01); *A61B 5/0031* (2013.01); *A61B 5/0422* (2013.01); *A61B 5/076* (2013.01); *A61B 5/1122* (2013.01); *A61N 1/37211* (2013.01); *A61N 1/37252* (2013.01); *H04B 5/0037* (2013.01); *H04M 1/0202* (2013.01); *H04Q 9/00* (2013.01); *H04W 4/027* (2013.01); *A61B 2560/029* (2013.01); *A61B 2562/0219* (2013.01); *G08C 2201/93* (2013.01); *H04Q 2209/88* (2013.01)

(58) Field of Classification Search
CPC .... H04M 11/007; A61B 5/0422; A61B 5/076; H04W 4/027; H04B 5/0037
See application file for complete search history.

(56) References Cited

U.S. PATENT DOCUMENTS

| | | |
|---|---|---|
| 8,509,882 B2 | 8/2013 | Albert et al. |
| 8,965,402 B2 | 2/2015 | Vathsangam et al. |
| 9,186,089 B2 | 11/2015 | Mazar et al. |
| 9,215,075 B1 | 12/2015 | Poltorak |
| 2001/0031998 A1 | 10/2001 | Nelson et al. |

(Continued)

OTHER PUBLICATIONS

Extended European Search Report for corresponding European application No. EP 18159362.5, dated Jul. 30, 2018.

*Primary Examiner* — Qun Shen
(74) *Attorney, Agent, or Firm* — Notaro, Michalos & Zaccaria P.C.

(57) ABSTRACT

A method for interaction with a medical device that is implanted in a body of a patient. The method includes detecting, using an inertial sensor, an arcuate motion of a wireless communication device terminating in physical contact between the wireless communication device and the body. In response to the detected arcuate motion, a wireless communication link is actuated between the wireless communication device and a transmitter in the implanted medical device. The wireless communication device data receives transmitted over the wireless communication link by the transmitter.

18 Claims, 2 Drawing Sheets

(56) References Cited

U.S. PATENT DOCUMENTS

| | | |
|---|---|---|
| 2003/0149459 A1 | 8/2003 | Von Arx et al. |
| 2006/0290496 A1 | 12/2006 | Peeters |
| 2007/0259689 A1 | 11/2007 | Kutaragi |
| 2010/0010392 A1 | 1/2010 | Skelton et al. |
| 2010/0292556 A1 | 11/2010 | Golden |
| 2011/0093287 A1 | 4/2011 | Dicks et al. |
| 2011/0288379 A1 | 11/2011 | Wu |
| 2012/0092156 A1* | 4/2012 | Tran .................... G06F 19/3418 340/539.12 |
| 2012/0191147 A1 | 7/2012 | Rao et al. |
| 2012/0225635 A1 | 9/2012 | Esbensen |
| 2013/0063344 A1 | 3/2013 | Obermuller et al. |
| 2014/0142403 A1 | 5/2014 | Brumback et al. |
| 2014/0156308 A1 | 6/2014 | Ohnemus et al. |
| 2014/0228649 A1 | 8/2014 | Rayner et al. |
| 2014/0266787 A1* | 9/2014 | Tran .................... A61B 5/0022 340/870.07 |
| 2014/0288435 A1 | 9/2014 | Richards et al. |
| 2015/0346834 A1 | 12/2015 | Martinez Fernandez et al. |
| 2016/0243373 A1* | 8/2016 | Kalgren ................ A61B 5/7475 |
| 2016/0250490 A1* | 9/2016 | Hoffman ............ A61N 1/37252 607/60 |
| 2016/0302692 A1* | 10/2016 | Demmer ................ A61B 5/061 |
| 2018/0014113 A1* | 1/2018 | Boesen ................ H04R 1/1091 |

* cited by examiner

REMOTE CONTROL AND INTERACTION WITH IMPLANTED DEVICES

FIELD OF THE INVENTION

The present invention relates generally to invasive medical devices, and particularly to methods, apparatus and software for wireless communication with implanted devices.

BACKGROUND

Various sorts of implantable monitoring devices are known in the art. ("Implantable" in this context includes devices that are inserted under the patient's skin, as well as deeper inside the body.) For example, Medtronic (Minneapolis, Minn.) produces the Reveal™ XT Insertable Cardiac Monitor (ICM), which is implanted under the skin of the chest and captures ECG information that can be useful in diagnosing cardiac arrhythmias. The ICM transfers data on demand via wireless link to a nearby receiver.

There have been a number of suggestions in the patent literature to provide implantable medical devices with generic wireless interfaces, enabling communication with standard sorts of communication devices, such as smartphones. For example, U.S. Pat. No. 9,215,075 describes systems and methods for supporting encrypted communications with a medical device, such as an implantable device, through a relay device to a remote server. An implantable medical device is generally constrained to employ a low-power transceiver, which supports short-distance digital communications. A relay device, such as a smartphone or Wi-Fi access point, acts as a conduit for the communications to the internet or other network. The medical device negotiates a secure channel through a smartphone or router, for example, which provides application support for the communication, but may be isolated from the content.

SUMMARY

Embodiments of the present invention that are described hereinbelow provide improved methods, apparatus and software for interacting with implanted medical devices.

There is therefore provided, in accordance with an embodiment of the invention, a method for interaction with a medical device that is implanted in a body of a patient. The method includes detecting, using an inertial sensor, an arcuate motion of a wireless communication device terminating in physical contact between the wireless communication device and the body. In response to the detected arcuate motion, a wireless communication link is actuated between the wireless communication device and a transmitter in the implanted medical device. The wireless communication device receives data transmitted over the wireless communication link by the transmitter.

In a disclosed embodiment, detecting the arcuate motion includes sensing an abrupt deceleration indicating that the wireless communication device has made the physical contact with the body.

In one embodiment, the medical device is implanted in a chest of the patient, and the arcuate motion terminates in contact between the wireless communication device and the chest.

In some embodiments, the data includes information gathered by the medical device with respect to physiological activity in the body. In one embodiment, the method includes performing in the wireless communication device an analysis of the received information, and outputting a result of the analysis.

In a disclosed embodiment, the wireless communication device includes a mobile telephone, and the method includes transmitting at least a part of the received data from the mobile telephone over a communication network to a server.

Additionally or alternatively, when the medical device includes a rechargeable power source, the method may include, upon actuating the wireless communication link, transmitting energy from the wireless communication device toward the medical device inside the body in order to recharge the power source.

There is also provided, in accordance with an embodiment of the invention, a computer software product for interaction with a medical device that is implanted in a body of a patient. The product includes a non-transitory computer-readable medium in which program instructions are stored. The instructions, when read by a processor in a wireless communication device that includes an inertial sensor, cause the processor to detect, using the inertial sensor, an arcuate motion of the wireless communication device terminating in physical contact between the wireless communication device and the body, and to actuate, in response to the detected arcuate motion, a wireless communication link between the wireless communication device and a transmitter in the implanted medical device, and to receive data transmitted over the wireless communication link by the transmitter.

There is additionally provided, in accordance with an embodiment of the invention, a wireless communication device for interaction with a medical device that is implanted in a body of a patient. The wireless communication device includes a wireless communication interface, an inertial sensor, and a processor, which is configured to detect, using the inertial sensor, an arcuate motion of the wireless communication device terminating in physical contact between the wireless communication device and the body, and to actuate, in response to the detected arcuate motion, the wireless communication interface to communicate with a transmitter in the implanted medical device, and to receive via the wireless communication interface data transmitted by the transmitter.

The present invention will be more fully understood from the following detailed description of the embodiments thereof, taken together with the drawings in which:

DETAILED DESCRIPTION OF EMBODIMENTS

To reduce size and battery consumption, implanted medical devices, such as implantable heart monitors, are commonly subject to tight constraints on computing power, memory, and communication bandwidth and range. Therefore, for purposes of data output and control, many such devices are coupled with a dedicated reader, which is held or fixed outside the body in proximity to the implanted device.

This configuration requires that the patient or a caregiver power on, set up, and position the reader properly whenever data readout is desired.

Embodiments of the present invention that are described herein obviate the need for a dedicated reader and enable essentially instant set up and actuation for data readout from an implanted medical device. In these embodiments, interaction with the implanted device is initiated by a single, simple and intuitive gesture, which is detected automatically by an inertial sensor in a wireless communication device that is to perform the data readout. Thus, readout can be initiated immediately when needed, even in stressful emergency situations. This sort of functionality can be implemented by a suitable software application running on a standard smartphone, although the principles of the present invention may be applied in improving the ease of use of dedicated readers, as well.

In the disclosed embodiments, the inertial sensor in a wireless communication device is used to detect a gesture comprising an arcuate motion of the device, which terminates in physical contact between the wireless communication device and the body. This physical contact may be sensed as an abrupt deceleration of the arcuate motion. This sort of motion will occur, for example, when a user holding the wireless communication device in his hand makes a gesture that brings the device around and into contact with his body in proximity to the implanted medical device. In response to the detected gesture, software running on the wireless communication device actuates a wireless communication link between the device and a transmitter in the implanted medical device, and then receives data transmitted over the wireless communication link by the transmitter.

Figure 1:
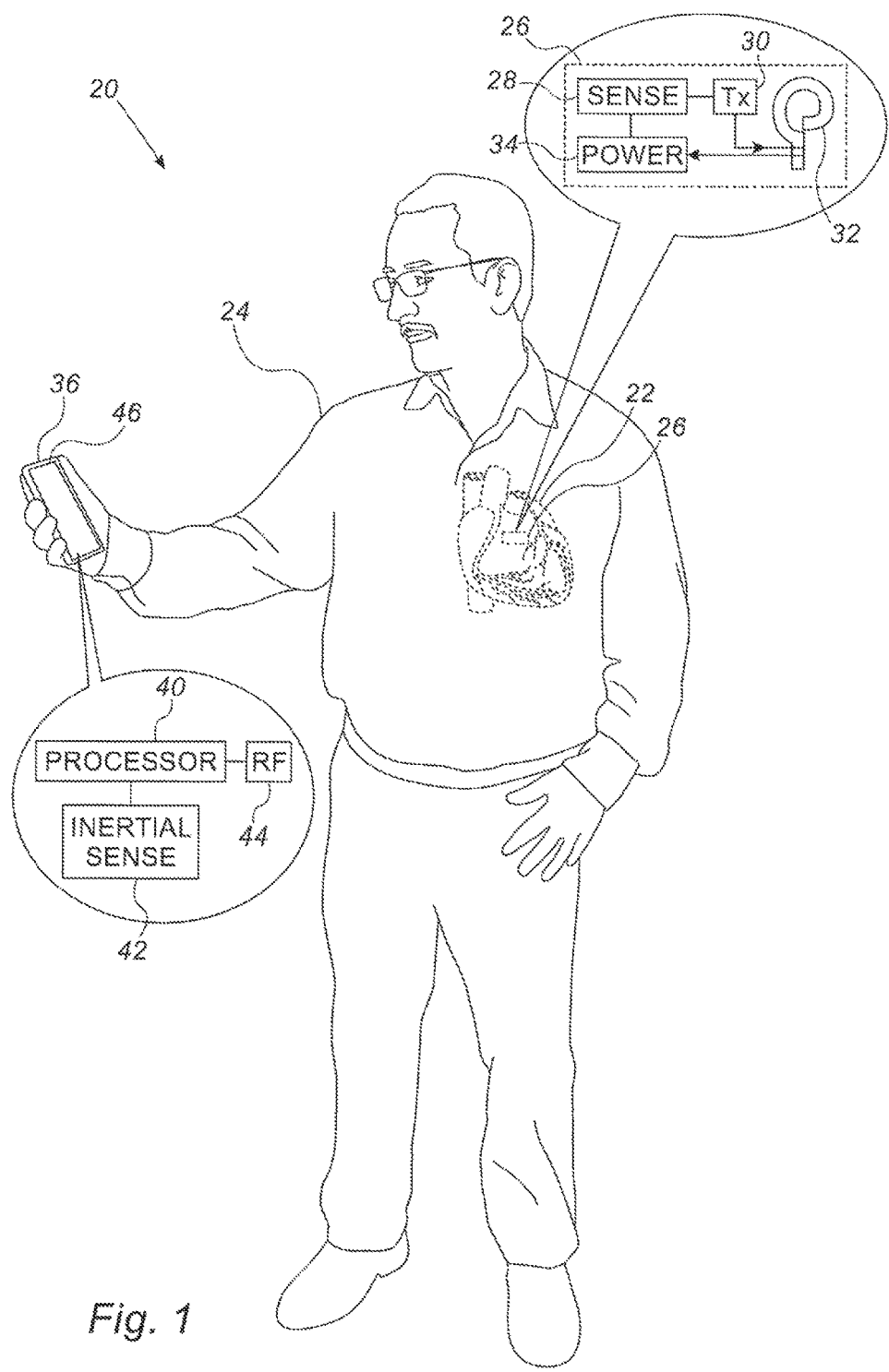
FIG. 1 is a schematic pictorial illustration of a system for heart monitoring, in accordance with an embodiment of the invention.
Figure 2:
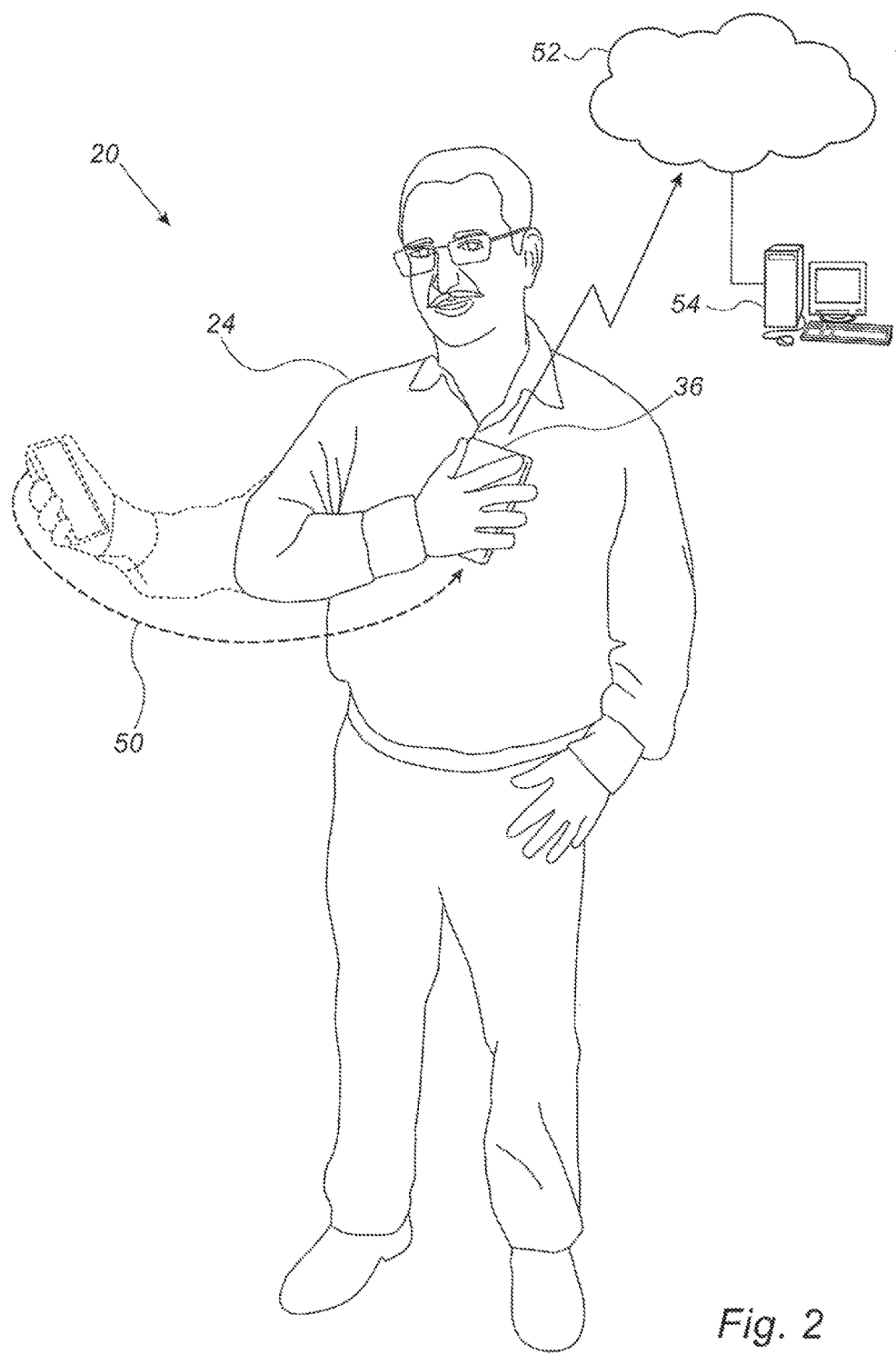
FIG. 2 a schematic pictorial illustration of a gesture used to activate communication in a system for heart monitoring, in accordance with an embodiment of the invention.

Reference is now made to FIGS. 1 and 2, which are schematic pictorial illustrations of a system 20 for heart monitoring, in accordance with an embodiment of the invention. FIG. 1 shows system 20 in an initial position, before actuation (with insets showing functional components of the elements of the system). FIG. 2 illustrates a gesture that can be used to actuate the system. System 20 is built around an implantable heart monitoring device 26, but the principles of this embodiment may similarly be applied, mutatis mutandis, to interaction with other sorts of implantable devices that are known in the art, which may be implanted in the chest or in other parts of the body.

In the present example, device 26 is implanted, typically via an incision or injection through the skin, in the chest of a patient 24 in proximity to a heart 22 that is to be monitored. Device 26 comprises a sensor 28, typically comprising an electrode or electrodes, which senses and records physiological activity, such as electrical signals generated by heart 22. When actuated, a transmitter 30 transmits recorded signal data via an integral antenna 32, represented in the figure as a coil. A power source 34, such as a battery and/or chargeable capacitor, supplies operating power to sensor 28 and transmitter 30, and may be rechargeable by means of radio-frequency (RF) energy received via antenna 32.

Patient 24 operates a smartphone 36 to receive and analyze the data transmitted by transmitter 30. Smartphone 36 is a standard, off-shelf device with mobile telephony, sensing, and processing capabilities. For the sake of brevity, only those elements of smartphone 36 that are directly relevant to interaction with implantable device 26 are described here. In the pictured example, smartphone 36 comprises a processor 40, along with an inertial sensor 42 and a short-range RF transceiver 44, such as a Bluetooth® or RF identification (RFID) transceiver. Smartphone 36 also comprises a user interface 46, comprising a touchscreen, as well as audio input and output.

Processor 40 carries out the functions that are described herein under the control of software, which is stored in a tangible, non-transitory memory (not shown), such as semiconductor, optical or magnetic memory. Typically, the software is in the form of an application program, which is downloaded to smartphone 36 in electronic form, over a network, although the software may alternatively be pre-installed in the smartphone or supplied on tangible media. After installation, patient or another user opens the application so that processor 40 will be ready to collect data from implanted device 26 on demand.

To initiate data transmission, patient 24 performs a gesture represented by an arrow 50 in FIG. 2: The patient (or possibly a caregiver alongside the patient) moves the hand holding smartphone 36 in an arc, terminating in physical contact between the smartphone and the patient's chest at a location near heart 22. Inertial sensor 42 will accordingly detect arcuate motion of smartphone 36 at a certain velocity, for example in the range of 20-200 cm/sec, with abrupt deceleration when the smartphone contacts the chest. "Abrupt" in this context means that the velocity of the smartphone decreases from at least 20 cm/sec to zero in 100 ms or less.

Upon sensing this particular pattern of motion, processor 40 immediately actuates transceiver 44 to begin receiving data from transmitter 30 in implanted device 26. For example, transceiver 44 may send a brief interrogation signal to device 26, which causes transmitter 30 to transmit a certain amount of data. Upon receiving the data, processor 40 may perform an analysis of the received information, and output the result. For example, processor 40 may output a graphical image and/or sound via user interface 46 to inform patient 24 that his cardiac activity is normal, or alternatively that a possible arrhythmia has been detected and that the patient should seek medical care. Additionally or alternatively, processor 40 may output at least a part of the received data and/or results of analysis via a communication network 52 (such as a cellular or Wi-Fi data network) to a server 54.

As another option, in embodiments in which power source 34 is rechargeable, transceiver 44 may also transmit RF energy to antenna 32 in order to charge the power source when the wireless communication link is actuated. Power source 34 rectifies and stores the energy in order to drive sensor 28 and transmitter 30. Thus, the useful lifetime of device 26 inside the body may be extended by recharging power source 34 every time transmitter 30 is interrogated.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for interaction with a medical device that is implanted in a body of a patient, the method comprising:

detecting, using an inertial sensor, an arcuate motion of a wireless communication device at a velocity in the range of 20-200 cm/sec, with abrupt deceleration terminating in physical contact between the wireless communication device and the body;

in response to the detected arcuate motion, actuating a wireless communication link between the wireless communication device and a transmitter in the implanted medical device; and receiving in the wireless communication device data transmitted over the wireless communication link by the transmitter, wherein the inertial sensor is adapted to actuate the wireless communication only in response to an arcuate motion of a wireless communication device at a velocity in the range of 20-200 cm/sec, wherein abrupt deceleration occurs when the velocity of the wireless communication device decreases from at least 20 cm/sec to zero in 100 ms or less.

2. The method according to claim 1, wherein the medical device is implanted in a chest of the patient, and wherein the arcuate motion terminates in contact between the wireless communication device and the chest.

3. The method according to claim 1, wherein receiving the data comprises receiving information gathered by the medical device with respect to physiological activity in the body.

4. The method according to claim 3, and comprising performing in the wireless communication device an analysis of the received information, and outputting a result of the analysis.

5. The method according to claim 1, wherein the wireless communication device comprises mobile telephone, and wherein the method comprises transmitting at least a part of the received data from the mobile telephone over a communication network to a server.

6. The method according to claim 1, wherein the medical device includes a rechargeable power source, and wherein the method includes, upon actuating the wireless communication link, transmitting energy from the wireless communication device toward the medical device inside the body in order to recharge the power source.

7. A computer software product for interaction with a medical device that is implanted in a body of a patient, the product comprising a non-transitory computer-readable medium in which program instructions are stored, which instructions, when read by a processor in a wireless communication device that includes an inertial sensor, cause the processor to detect, using the inertial sensor, an arcuate motion of the wireless communication device at a velocity in the range of 20-200 cm/sec, with abrupt deceleration terminating in physical contact between the wireless communication device and the body, and to actuate, in response to the detected arcuate motion, a wireless communication link between the wireless communication device and a transmitter in the implanted medical device, and to receive data transmitted over the wireless communication link by the transmitter, wherein the inertial sensor is adapted to actuate the wireless communication only in response to an arcuate motion of a wireless communication device at a velocity in the range of 20-200 cm/sec, wherein abrupt deceleration occurs when the velocity of the wireless communication device decreases from at least 20 cm/sec to zero in 100 ms or less.

8. The product according to claim 7, wherein the medical device is implanted in a chest of the patient, and wherein the arcuate motion terminates in contact between the wireless communication device and the chest.

9. The product according to claim 7, wherein the data comprise information gathered by the medical device with respect to physiological activity in the body.

10. The product according to claim 9, wherein the instructions cause the processor to perform an analysis of the received information, and to output a result of the analysis.

11. The product according to claim 7, wherein the wireless communication device comprises mobile telephone, and wherein the instructions cause the processor to transmit at least a part of the received data from the mobile telephone over a communication network to a server.

12. The product according to claim 7, wherein the medical device includes a rechargeable power source, and wherein the instructions cause the processor, upon actuation of the wireless communication link, to transmit energy from the wireless communication device toward the medical device inside the body in order to recharge the power source.

13. A wireless communication device for interaction with a medical device that is implanted in a body of a patient, the wireless communication device comprising:

a wireless communication interface; an inertial sensor; and a processor, which is configured to detect, using the inertial sensor, an arcuate motion of the wireless communication device at a velocity in the range of 20-200 cm/sec, with abrupt deceleration terminating in physical contact between the wireless communication device and the body, and to actuate, in response to the detected arcuate motion, the wireless communication interface to communicate with a transmitter in the implanted medical device, and to receive via the wireless communication interface data transmitted by the transmitter, wherein the inertial sensor is adapted to actuate the wireless communication only in response to an arcuate motion of a wireless communication device at a velocity in the range of 20-200 cm/sec, wherein abrupt deceleration occurs when the velocity of the wireless communication device decreases from at least 20 cm/sec to zero in 100 ms or less.

14. The wireless communication device according to claim 13, wherein the medical device is implanted in a chest of the patient, and wherein the arcuate motion terminates in contact between the wireless communication device and the chest.

15. The wireless communication device according to claim 13, wherein the data comprise information gathered by the medical device with respect to physiological activity in the body.

16. The wireless communication device according to claim 15, wherein the processor is configured to perform an analysis of the received information, and to output a result of the analysis.

17. The wireless communication device according to claim 13, wherein the wireless communication device comprises a mobile telephone, and wherein the processor is configured to transmit at least a part of the received data from the mobile telephone over a communication network to a server.

18. The wireless communication device according to claim 13, wherein the medical device includes a rechargeable power source, and wherein the wireless communication interface is configured, upon actuation of the wireless communication link, to transmit energy from the wireless communication device toward the medical device inside the body in order to recharge the power source.

* * * * *